United States Patent [19]
Werner

[11] Patent Number: 6,103,197
[45] Date of Patent: Aug. 15, 2000

[54] METHOD AND APPARATUS FOR OPTICALLY DETERMINING TOTAL HEMOGLOBIN CONCENTRATION

[75] Inventor: Ziegler Werner, Graz, Austria

[73] Assignee: AVL Medical Instruments AG, Schaffhausen, Switzerland

[21] Appl. No.: 09/031,918

[22] Filed: Feb. 27, 1998

Related U.S. Application Data

[62] Division of application No. 08/892,126, Jul. 14, 1997, Pat. No. 5,773,301.

[30] Foreign Application Priority Data

Jul. 12, 1996 [AT] Austria ..................................... 1262/96

[51] Int. Cl.$^7$ ................................................. G01N 21/00
[52] U.S. Cl. .................. 422/82.09; 356/39; 356/433; 436/68; 436/164
[58] Field of Search .................. 422/82.05, 82.09; 436/66, 68, 164; 356/39, 433, 436

[56] References Cited

U.S. PATENT DOCUMENTS

| | | |
|---|---|---|
| 4,076,420 | 2/1978 | DeMaeyer et al. . |
| 4,676,640 | 6/1987 | Briggs . |
| 5,061,632 | 10/1991 | Shephard et al. . |
| 5,064,282 | 11/1991 | Curtis . |
| 5,127,406 | 7/1992 | Yamaguchi . |
| 5,492,833 | 2/1996 | Rodriguez et al. . |
| 5,525,518 | 6/1996 | Lundsgaard et al. . |
| 5,770,454 | 6/1998 | Essenpreis et al. . |
| 5,835,649 | 11/1998 | Turner et al. . |

FOREIGN PATENT DOCUMENTS

| | | |
|---|---|---|
| 56271 | 12/1990 | Austria . |
| 203632 | 10/1983 | Germany . |

OTHER PUBLICATIONS

S. Takatani et al. "A Miniature Hybrid Reflection Type Optical Sensor . . . Whole Blood" in IEEE, vol. 35, No. 3, Mar. 1988.

International Patent Publication No. WO 94/08237 to A. Shepherd et al. entitled Method and Apparatus for Direct Spectrophotometric Measurements in Unaltered Whole Blood, dated Apr., 1994.

*Primary Examiner*—Jeffrey Snay
*Attorney, Agent, or Firm*—Watson Cole Grindle Watson, P.L.L.C.

[57] ABSTRACT

In a method of optically determining the total hemoglobin concentration (tHb) in non-hemolyzed whole blood, using at least two wavelengths for measuring, a first wavelength of $\lambda < 805$ nm and a second wavelength of $\lambda > 805$ nm is employed, such that the following is valid for the absorption coefficients of the hemoglobin derivatives $O_2Hb$ and RHb at the two measurement wavelengths $\lambda_1$ and $\lambda_2$: $\sigma O(\lambda_1) \sim \sigma R(\lambda_2)$ and $\sigma R(\lambda_1) \sim \sigma O(\lambda_2)$. The sum of absorption values $A_1$ and $A_2$ measured at wavelengths $\lambda_1$ and $\lambda_2$ will be a quantity which is proportional to the total hemoglobin concentration tHb and independent of the oxygen saturation $O_{2sat}$.

9 Claims, 4 Drawing Sheets

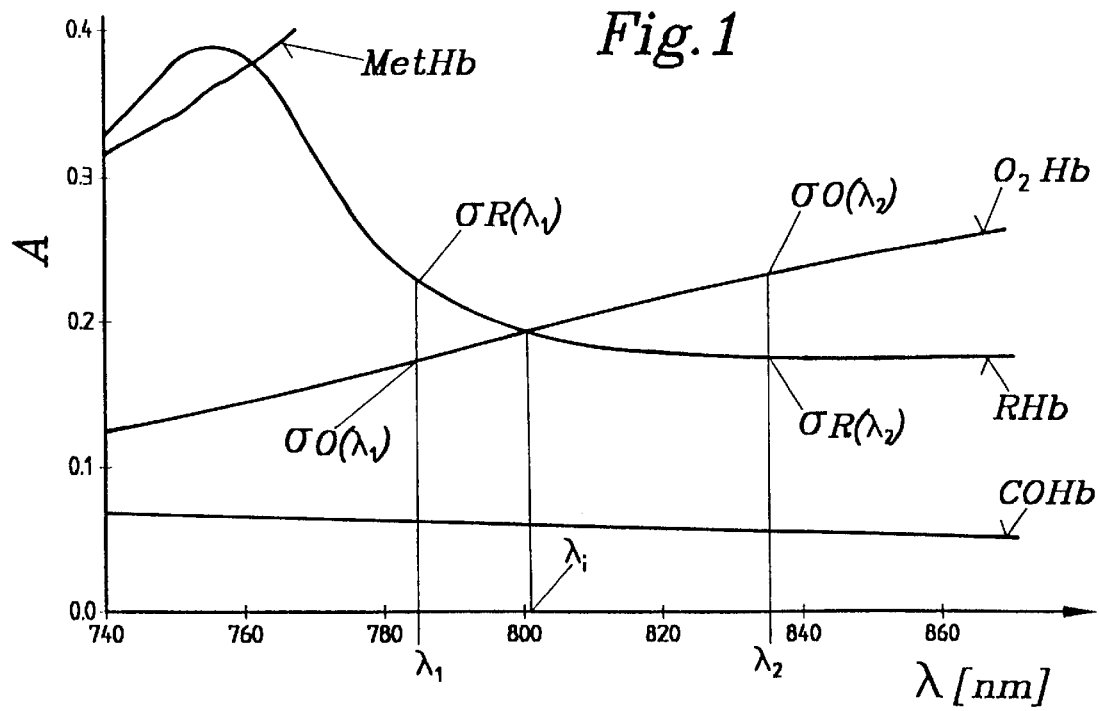
*Fig. 1*
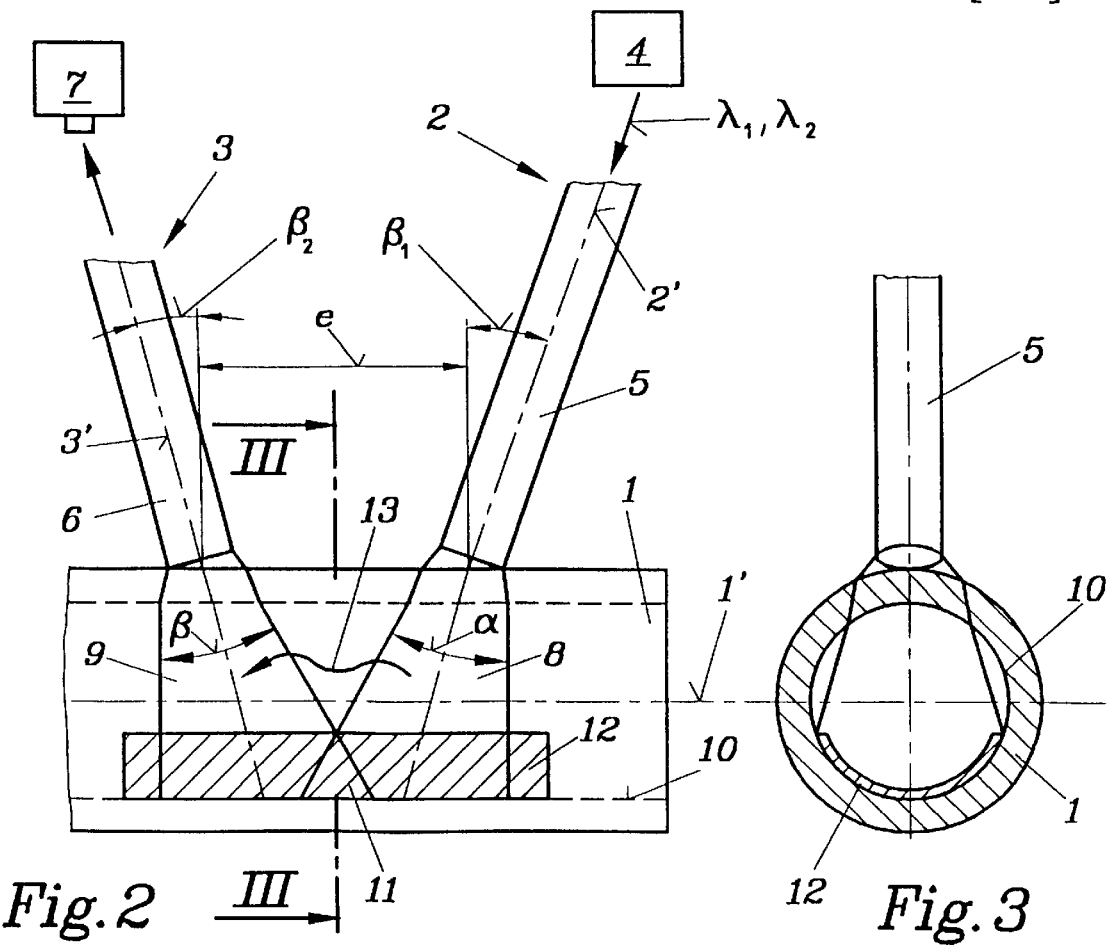
*Fig. 2*  *Fig. 3*

METHOD AND APPARATUS FOR OPTICALLY DETERMINING TOTAL HEMOGLOBIN CONCENTRATION

CROSS-REFERENCE TO RELATED APPLICATION

This is a divisional of application Ser. No. 08/892,126, filed Jul. 14, 1997, now U.S. Pat. No. 5,773,301.

BACKGROUND OF THE INVENTION

The present invention relates to a method of optically determining the total hemoglobin concentration as well as the oxygen saturation in non-hemolyzed whole blood, using at least two measurement wavelengths, and an apparatus for implementing the method of the invention.

Abbreviations used are as following:

Hb . . . hemoglobin tHb . . . total hemoglobin concentration (total of all active and inactive hemoglobin derivatives in the blood)

$O_{2sat}$ . . . percent oxygen saturation $O_2Hb$ . . . oxygenized Hb

RHb . . . deoxygenized Hb

COHb . . . carboxy Hb

MetHb . . . methemoglobin

SulfHb . . . sulfhemoglobin

σO . . . absorption coefficient of $O_2Hb$

σR . . . absorption coefficient of RHb

σC . . . absorption coefficient of COHb

σM . . . absorption coefficient of MetHb $C_O$ . . . concentration of $O_2Hb$ $C_R$ . . . concentration of RHb $C_C$ . . . concentration of COHb

DESCRIPTION OF THE PRIOR ART

A method and apparatus of the above type are discussed in U.S. Pat. No. 5,061,632, for instance. The oximeter described therein for measuring tHB and $O_{2sat}$ is provided with a capillary tube containing a sample of non-hemolyzed whole blood, which tube may be inserted into the center bore of a cylindrical evaluation unit. Spaced along the axis of the center bore the evaluation unit has two radial bores positioned at a right angle relative to the center bore, through which the measuring radiation emitted by two LEDs is supplied. In axial direction between the two radial light entrance bores another radial bore is positioned normal to the center bore, through which the light emitted by the sample is passed to a detector placed on the wall of the cylindrical evaluation unit. The first diode emits infrared radiation having a wavelength of some 800 nm, and is used to determine the tHb. In order to obtain a measurement that is largely independent of the ratio between $O_2$ and RHb, it is performed as close as possible to the isosbestic point of the absorption coefficients of $O_2Hb$ and RHb, i.e., at a wavelength of 805 nm, approximately (see IEEE Transactions on Biomedical Engineering, vol. 35, No. 3, March 1988). The second diode emits red light having a wavelength of 660 nm and serves to determine the oxygen saturation $O_{2sat}$, as there is a significant difference at this wavelength between the absorption coefficients for $O_2Hb$ and RHb. The contributions of the remaining hemoglobin derivatives (COHb, metHb, sulfHb) are ignored by the above method. As a consequence, determination of $O_{2sat}$ is subject to an error of about 1–15%.

A disadvantage of the method described in U.S. Pat. No. 5,061,632 is that no standard light sources are available exactly at the isosbestic point of $\lambda_i$=805 nm, and that even small deviations from the isosbestic point due to the opposed curves of σO and σR in this range may lead to errors in determining tHb and $O_{2sat}$.

Other known methods of determining the total hemoglobin concentration include (1) Absorption measurements employing Lambert-Beer's law Absorption measurements are performed at a defined number of measurement wavelengths. A linear equation system is evaluated, which may be overdetermined by using several wavelengths in order to increase measuring accuracy. For measurements employing Lambert-Beer's law a homogeneous medium is required, i.e., only hemolyzed blood may be used; otherwise, LambertBeer's law is valid only approximately.

(2) In WO 94/08237 a method and apparatus are described for direct spectrophotometric measurements in undiluted whole blood, where wavelengths $\lambda_1$ to $\lambda_n$ are radiated into the sample and detected at a large detection angle. Absorption is thus measured at a defined number of wavelengths, with due consideration to the scattered portion of the irradiated light. The disadvantage of this method is that a nonlinear equation system must be solved where the degree of nonlinearity is dependent on the sample depth.

In general, reproducible results are obtained with such measuring methods only if there are no changes in the optical path. Changes are mainly caused by differences in light entrance and exit losses, as the length of path through the sample is undefined in scattered light measurements. If a replaceable cuvette or cartridge (oneway sensor) is used, the light entrance and exit factors are not accurately reproducible due to the varying nonplanar surfaces of the individual cuvettes or cartridges (polarization effects, scattering, etc.).

In DD 203 632 A, a rapid method and device are presented for photometric determination of the concentration of CO—Hb. Two wavelengths are employed for measuring, the light sources being luminescence diodes with maximum spectral emissions at 565 nm and 940 nm. The light receivers are solid state photodetectors, which are directed onto the sample provided as a special filtering paper soaked with the test material. Spectral absorption is measured by evaluation of the remission and/or transmission, the CO—Hb concentration being determined by a computer.

In AT-E 56 271 B a method for spectrophotometric determination of the concentrations of a number of hemoglobin derivatives in whole blood is described, where several different wavelengths are radiated into the blood sample and absorption values are measured. The concentrations of the individual hemoglobin derivatives are determined from a system of equations.

Other photometric methods of measuring blood components are discussed in U.S. Pat. Nos. 5,127,406 and 5,064,282.

SUMMARY OF THE INVENTION

It is an object of the present invention to propose a method and apparatus for optically determining the total hemoglobin concentration in non-hemolyzed whole blood, which will yield useful measured results while offering simplicity of design and computing operations. Another concern of the invention is that it should also permit determination of the oxygen saturation and should be suitable for use with replaceable oneway cartridges, while solving the problem of varying light entrance and exit losses.

In the invention this object is achieved by employing a first measurement wavelength of $\lambda_1 < 805$ nm and a second measurement wavelength of $\lambda_2 > 805$ nm such that the following is valid for the absorption coefficients of the hemoglobin derivatives $O_2Hb$ and $RHb$ at the two measurement wavelengths $\lambda_1$ and $\lambda_2$: $\sigma O(\lambda_1)$ equals approximately $\sigma R(\lambda_2)$ and $\sigma R(\lambda_1)$ equals approximately $\sigma O(\lambda_2)$, and that the absorption values $A_1$ and $A_2$ are measured at the wavelengths $\lambda_1$ and $\lambda_2$ and the sum of the two absorption values $A_1 + A_2$ is a quantity which is proportional to the total hemoglobin concentration tHb and independent of the oxygen saturation $O_{2sat}$. The method of the invention employs two isosbestically symmetric wavelengths, which are selected such that a measurement using conventional laser diodes will produce the same advantages as would be offered by performing a measurement directly at the isosbestic point. The absorption coefficients of $O_2Hb$ and $RHb$ should not differ from each other by more than ±5% at the two wavelengths $\lambda_1$ and $\lambda_2$. Moreover, the measurement is largely independent of the oxygen saturation of the sample.

For compensation of different excitation intensities $I_1$ and $I_2$ at wavelengths $\lambda_1$ and $\lambda_2$, the invention introduces a correction factor f, such that the total hemoglobin concentration tHb is proportional to the sum of $A_1 + fA_2$, factor f being between 0.5 and 2.0 and representing a calibrating variable dependent on the chosen measuring configuration.

Useful measurement wavelengths for $\lambda_1$ are between 780 and 790 nm, preferably at 785±3 nm, and for $\lambda_2$ between 830 and 850 nm, preferably at 836±3 nm. For use with the above wavelengths (780–785 nm, 840–850 nm) standard laser diodes are available, which will emit a sharply defined emission wavelength.

According to the invention the oxygen saturation $O_{2sat}$ may be approximately determined from the obtained absorption values $A_1$ and $A_2$, using the formula $O_{2sat}[\%]=$ $$=100.(\sigma R(\lambda_1).A_2-\sigma R(\lambda_2).A_1)/((A_1+A_2).(\sigma R(\lambda_1)-\sigma R(\lambda_2))).$$

This calculation of the oxygen saturation is based on the following considerations:

$$tHb=C_O+C_R+C_C \quad C_C<<C_O+C_R \Rightarrow C_C\sim 0$$

$$O_{2sat}[\%]=100.C_O/(C_O+C_R)\sim 100.C_O/tHb$$

$$A_1=\sigma R_1.C_R+\sigma O_1 C_O+\sigma C_1.C_C \text{ with } \sigma C_1.C_C\sim 0$$

$$A_2=\sigma R_2.C_R+\sigma O_2 C_O+\sigma C_2.C_C \text{ with } \sigma C_2.C_C\sim 0$$

$$\Rightarrow tHb=[A_1(\sigma R_2-\sigma O_2)+A_2(\sigma O_1-\sigma R_1)]/(\sigma R_2.\sigma O_1-\sigma R_1.\sigma O_2) \text{ with } \sigma R_1\sim \sigma O_2, \sigma R_2\sim \sigma O_1$$

$$\Rightarrow tHb=(A_1+A_2)/(\sigma R_2+\sigma R_1=K.(A_1+A_2)$$

$$C_O=(A_1\sigma R_2-A_2\sigma R_1)/(\sigma R_2.\sigma O_1-\sigma R_1.\sigma O_2)$$

$$O_{2sat}[\%]=100.(A_2\sigma R_1-A_1\sigma R_2)/[A_1+A_2)(\sigma R_1-\sigma R_2)]$$

It would further be possible to use a third wavelength for determination of the oxygen saturation. For this purpose any wavelength would be suitable at which absorption coefficients $\sigma R$ and $\sigma O$ exhibit differences for RHb and $O_2Hb$ which are as large as possible. An advantageous wavelength would be 680 nm (little influence of methb), for example.

A measuring apparatus of the invention for optically determining the total hemoglobin concentration in non-hemolyzed whole blood, comprising a capillary channel for holding a blood sample, and an excitation device for supplying at least two measurement wavelengths, and a detection device, where the optical axes of the excitation device and the detection device are directed towards the capillary channel and the excitation device has a cone of excitation light defined by an opening angle $\alpha$ and the detection device has a detection cone defined by an acceptance angle $\beta$, is improved in pursuance of one of the objects of the present invention, i.e., providing for an advantageous means of calibration, in such a manner that the inclination angles of the optical axes and the distance of these axes at the intersection points with the capillary channel are chosen with respect to the diameter of the capillary channel such that the excitation light cone and the detection cone overlap on the inner wall of the capillary channel if said capillary channel is filled with an aqueous solution, and that they do not overlap if said capillary channel is filled with whole blood, on account of the reduced mean penetration depth of the measurement radiation.

Due to the overlapping of excitation light cone and detection cone in a capillary tube filled with an aqueous solution, such as a calibrating solution, a dummy measurement may be performed in which the measuring light affected by entrance and exit losses will enter the detection device upon reflection at the inner wall of the capillary channel. Due to the use of at least two wavelengths for measurement the different optical losses may be detected before each measurement. For this purpose the inner wall of the capillary tube must exhibit different reflection values at the two wavelengths in order to permit useful calibration values to be obtained. This applies especially if, according to a preferred embodiment of the invention, the capillary channel is positioned in a oneway cartridge that can be inserted into an evaluation unit including the excitation and detection device.

In view of the wavelengths used for measurement it is an advantage to provide a red calibration surface on the inner wall of the capillary channel, at least in the region of the overlapping cones of detection and excitation light. It is of further advantage if the red calibration surface covers an area on the inner wall of the capillary channel that extends over some 20 to 40 percent of the circumference and is situated opposite of the excitation and detection device.

In another embodiment of the invention the proposal is put forward that the capillary channel be enlarged to form a measuring chamber in the region of the overlapping cones of excitation and detection light, one wall of said chamber being provided with an optical sensor whose cover layer, which is permeable to the parameter to be measured, should be configured as a red calibration surface. For example, the optical sensor may exhibit an indicator layer containing an indicator for $pO_2$ measurement in the whole blood sample.

BRIEF DESCRIPTION OF THE DRAWINGS

The invention will be further described with reference to the accompanying, partly schematical drawings, in which FIG. 1 is a diagram showing different absorptions of the individual hemoglobin derivatives as a function of wavelength.

FIG. 2 shows a first variant of a measuring apparatus according to the invention.

FIG. 3 shows the measuring apparatus of FIG. 2, as a section along line III—III in FIG. 2.

In FIG. 1 the different contributions of the individual hemoglobin derivatives RHb, $O_2Hb$, COHb and metHb are presented for wavelengths ranging from 740 to 880 nm. An isosbestic point for the main components RHb and $O_2$Hb is situated at $\lambda_i=805$ nm. As may further be seen, $\sigma R(\lambda_1)$ equals $\sigma O(\lambda_2)$, and $\sigma O(\lambda_1)$ equals $\sigma R(\lambda_2)$ for the wavelengths $\lambda_1=785$ nm and $\lambda_2=836$ nm entered in the drawing. Utilizing the above condition, the sum of the two absorption values $A_1$ and $A_2$ measured at wavelengths $\lambda_1$ and $\lambda_2$ will be proportional to the tHb of the blood sample and independent of the oxygen saturation. As is further seen from FIG. 1, the absorption coefficient of COHb will be approximately the same at both wavelengths, i.e., $\sigma C(\lambda_1)$ equals $\sigma C(\lambda_2)$. Due to the small value of the absorption coefficient for COHb and the low concentration of COHb, the product of these two factors may be neglected in a first approximation in calculating tHb.

FIGS. 2 and 3 show a first variant of a measuring apparatus of the invention for optically determining tHb in non-hemolyzed whole blood. The apparatus comprises a capillary channel 1 designed for containing a blood sample, an excitation device 2 for supplying at least two measurement wavelengths $\lambda_1$ and $\lambda_2$, and a detection device 3, the optical axes 2' and 3' of excitation device 2 and detection device 3 being directed towards the capillary channel 1. The excitation device 2 exhibits a unit 4 providing the two measurement wavelength $\lambda_1$ and $\lambda_2$, and light guiding means, such as an optical fiber 5 for light supply. Similarly, the detection device 3 includes an optical fiber 6 and a detector 7. Due to the numerical aperture of the optical fiber 5 the excitation device 2 is assigned a beam opening angle $\alpha$ for the excitation light cone 8. In the same way, the detection device 3 has a detection cone 9 defined by an acceptance angle $\beta$. The two cones 8 and 9 overlap on the inner wall 10 of the capillary channel 1 if the latter is filled with aqueous solution. In order to achieve a sufficiently large overlap region 11 of the two cones 8 and 9, at least one of axes 2' and/or 3' may be inclined relative to the normal on axis 1' of capillary channel 1 by the angle $\beta_1$ and/or $\beta_2$. By varying the distance e between the excitation device 2 and the detection device 3 and by modifying the two angles $\beta_1$ and $\beta_2$ it will be possible to optimize sensitivity during the measuring and calibrating process.

Figure 4:
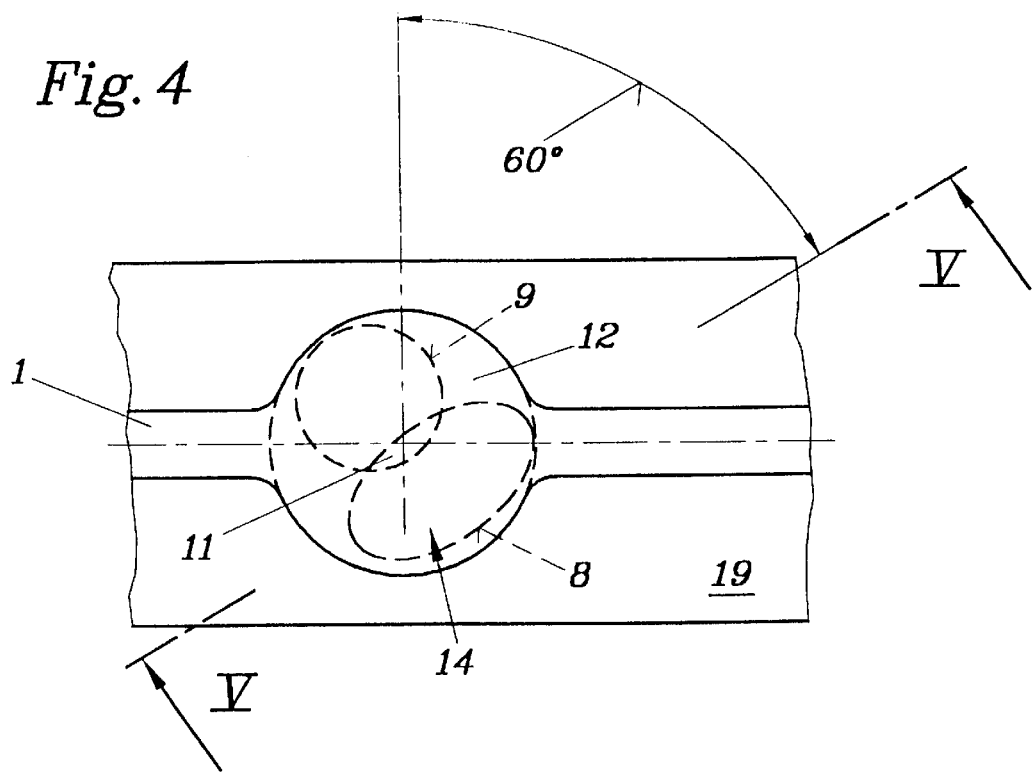
FIGS. 4 to 7 show another variant of the measuring apparatus of the invention.

For calibration of the measuring apparatus the inner wall 10 of the capillary channel 1 is provided with a red calibration surface 12, at least in the overlap region 11 of the two cones 8 and 9. This calibration surface 12 extends over some 20 to 40 percent of the circumference of the inner wall. The interior diameter of capillary tube 1 is 1 mm typically.

At the end of the calibrating process the capillary tube is filled with whole blood, which will limit the mean penetration depth of the measurement radiation to the upper half or upper third of the capillary tube. As a consequence, the two cones 8 and 9 will no longer overlap, such that the light scattered by the blood cells in the direction of arrow 13 will be measured.

Figure 5:
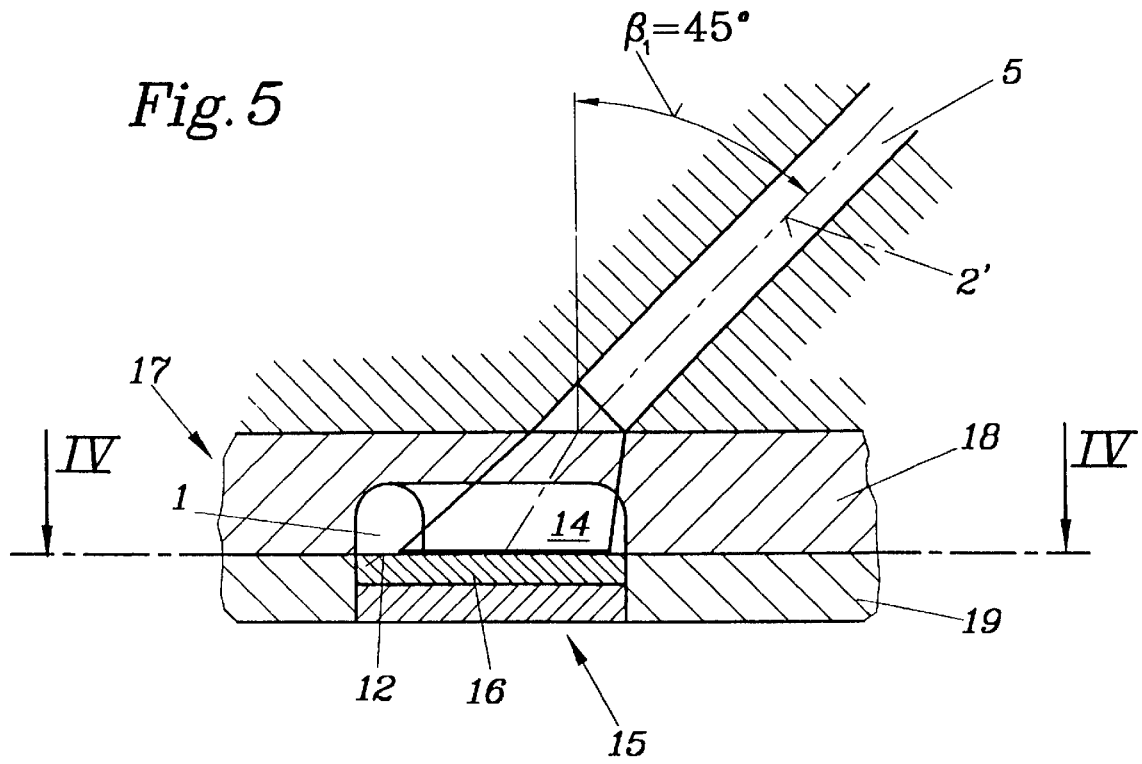

FIGS. 4 and 5 show a variant of the invention in which the capillary channel 1 widens to form a measuring chamber 14 in the region 11 of the overlapping cones of excitation and detection light 8 and 9, respectively, where the (for instance) circular base area of the measuring chamber 14 is provided with an optical sensor 15. This optical sensor 15 may contain an indicator in an indicator layer 16, for instance, to measure the $PO_2$, $pCO_2$, or pH of the whole blood sample, and may have an analyte-permeable cover layer simultaneously serving as red calibration surface 12. In the variant of FIGS. 4 and 5 the capillary channel 1 with the measuring chamber 14 is located in a oneway cartridge 17 configured in two parts 18 and 19, which may be inserted into an evaluation unit (not shown here in detail) provided with optical devices 2 and 3. FIG. 4 shows the overlap region 11 of excitation light cone 8 and detection cone 9.

Figure 6:
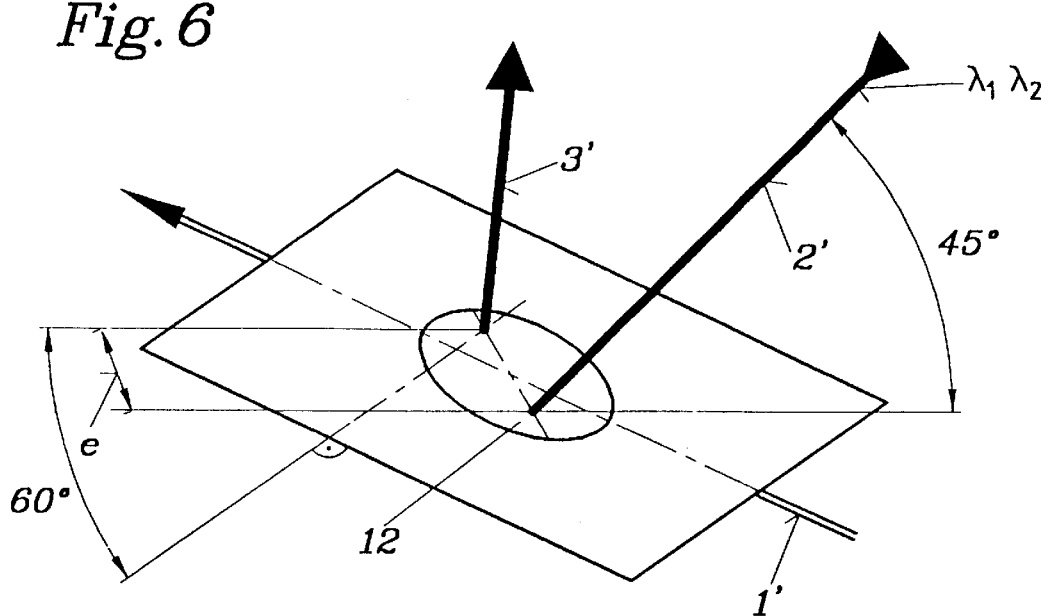
Figure 7:
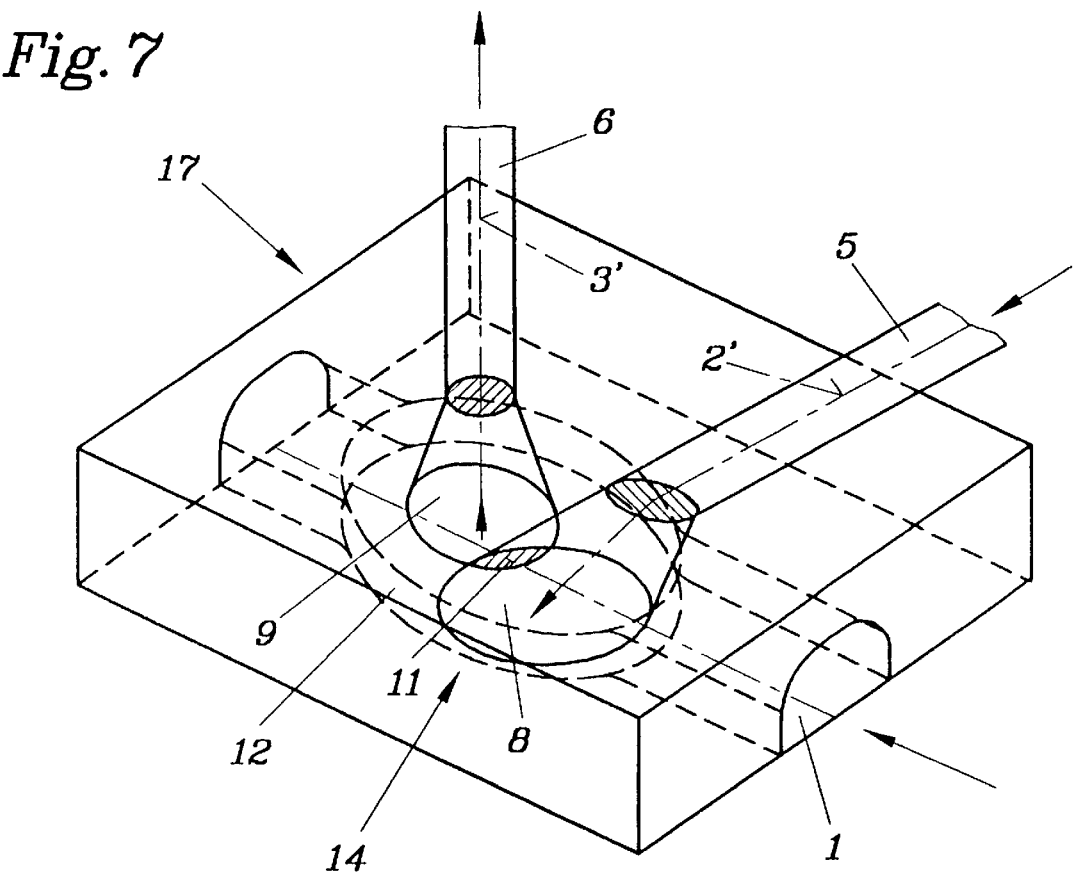

FIGS. 6 and 7 show the measuring apparatus according to FIGS. 4 and 5 in three-dimensional representation, FIG. 6 being solely concerned with the geometrical configuration. In FIG. 7 a flat capillary channel is shown, which widens to form a measuring chamber 14, thus enhancing the flow properties of the sample. The height of the capillary channel and the measuring chamber is approximately 0.7 mm, the penetration depth of the measurement radiation is approximately 0.3 mm in the instance of a capillary channel filled with whole blood.

During calibration the excitation light is entered into the cartridge 17 by means of the lightguide 5 and reflected at the calibration surface 12 in dependence of the specific wavelength. The reflected light is detected by the optical receiver. If at least two wavelengths are used at which the calibration surface 12 exhibits different absorption values and, consequently, different reflection values, it has been found that a calibration value may be obtained which is proportional to the light entrance and exit losses. The calibration value may be formed from the ratio of the reflection values of the two wavelengths used for measurement. This ratio must be within a given, predetermined range to permit calibration. In this way it will be possible to calibrate cartridge-specific light entrance losses prior to measurement. If more than two measurement wavelengths are used the accuracy of calibration may be improved accordingly.

Figure 8:
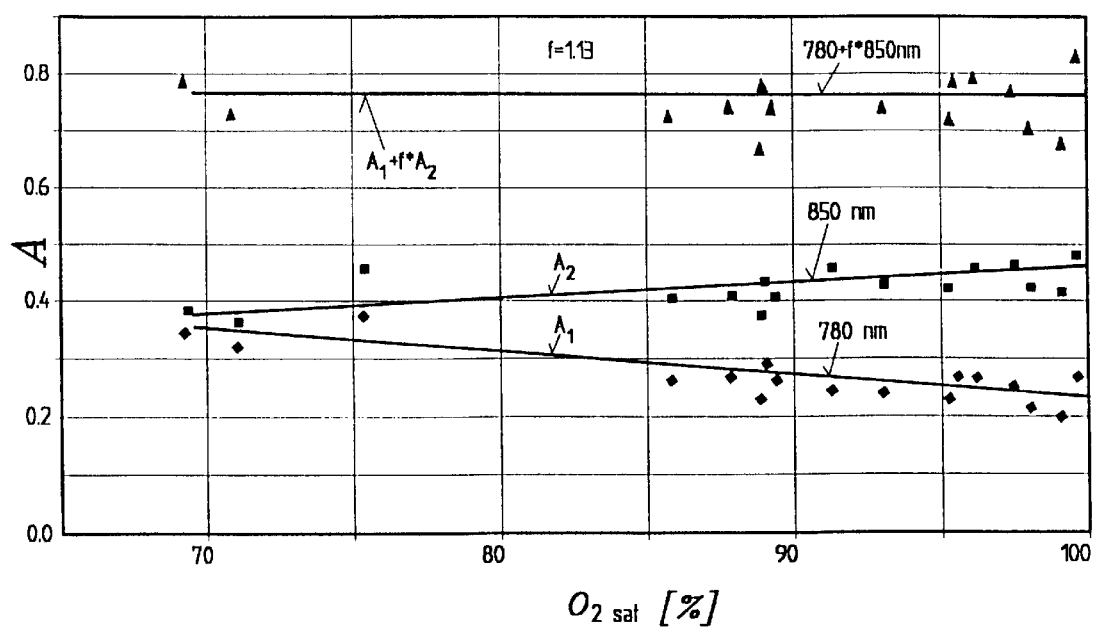
FIGS. 8 and 9 are diagrams showing a sum signal for tHb independent of $O_{2sat}$.
Figure 9:
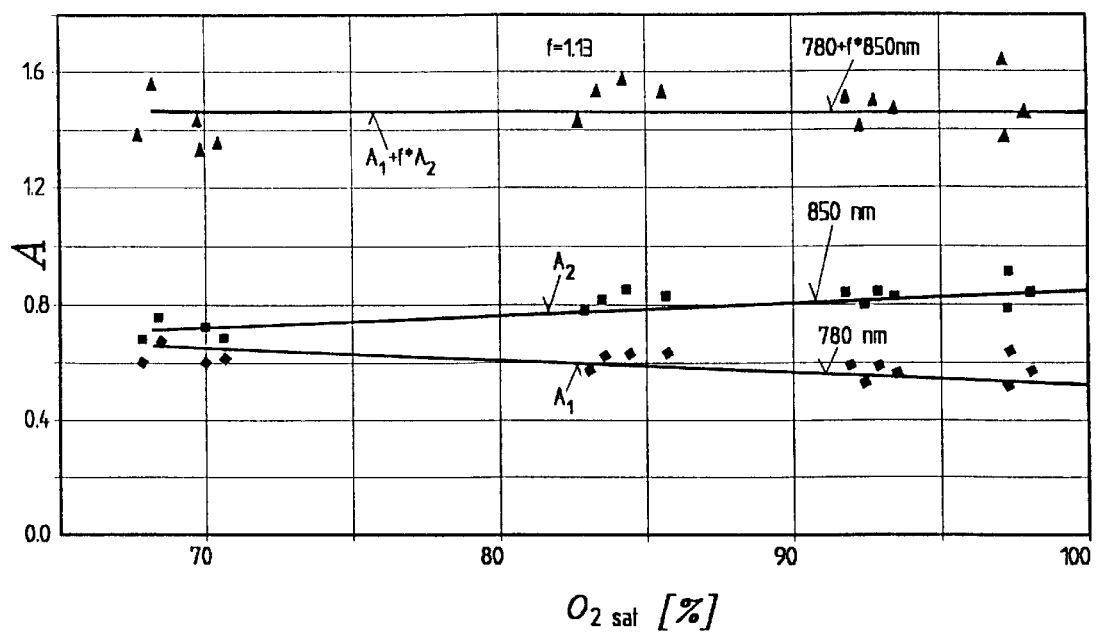

The digrams of FIGS. 8 and 9, where absorption A is plotted on the ordinate and oxygen saturation $O_{2sat}$ on the abscissa, show that the sum signal $A_1+f.A_2$ of absorption values $A_1$ and $A_2$ is constant at wavelengths $\lambda_1=780$ nm and $\lambda_2=850$ nm for different values of $O_{2sat}$. In FIG. 8, tHb=160 mg/ml, in FIG. 9, tHb=220 mg/ml. Factor f=1.13.

I claim:

1. Measuring apparatus for optically determining the total hemoglobin concentration (tHb) in non-hemolyzed whole blood, comprising a capillary channel for holding a blood sample, having an inner wall and an inner diameter, an excitation device for supplying at least first and second measurement wavelengths, defining a first optical axis directed towards said capillary channel and an excitation light cone defined by an opening angle $\alpha$, a detection device, defining a second optical axis directed towards said capillary channel and a detection light cone defined by an acceptance angle, wherein inclination angles $\beta_1$, $\beta_2$ of said first and second optical axes and a distance e of said axes at intersection points with said capillary channel are chosen with respect to said diameter of said capillary channel such that said excitation light cone and said detection cone light overlap on said inner wall of said capillay channel if said capillary channel is filled with an aqueous solution, and that they do not overlap if said capillary channel is filled with whole blood, on account of reduced mean penetration depth of first and second measurement wavelengths.

2. The apparatus of claim 1, wherein said inner wall of said capillary channel is provided with a red calibration surface, at least in a region where said detection light cone overlapps said excitation light cone.

3. The apparatus of claim 1, wherein said red calibration surface covers an area on said inner wall of said capillary channel that extends over some 20 to 40 percent of the circumference and is situated opposite of said excitation device and said detection device.

4. The apparatus of claim 2, wherein said capillary channel is enlarged to form a measuring chamber in a region where said detection light cone overlapps said excitation light cone, one wall of said measuring chamber being provided with an optical sensor having a cover layer, which is permeable to a parameter to be measured, and is configured as a red calibration surface.

5. The apparatus of claim 4, wherein said optical sensor exhibits an indicator layer containing an indicator for $pO_2$ measurement in non-hemolyzed whole blood.

6. The apparatus of claim 4, wherein said optical sensor exhibits an indicator layer containing an indicator for $pCO_2$ measurement in non-hemolyzed whole blood.

7. The apparatus of claim 4, wherein said optical sensor exhibits an indicator layer containing an indicator for pH measurement in non-hemolyzed whole blood.

8. The apparatus of claim 1, wherein said capillary channel is positioned in a oneway cartridge which is insertable into an evaluation unit including said excitation device and said detection device.

9. The apparatus of claim 4, wherein said capillary channel is positioned in a oneway cartridge which is insertable into an evaluation unit including said excitation device and said detection device.

* * * * *

UNITED STATES PATENT AND TRADEMARK OFFICE
CERTIFICATE OF CORRECTION

PATENT NO. : 6,103,197
DATED : August 15, 2000
INVENTOR(S) : Werner Ziegler

It is certified that error appears in the above-identified patent and that said Letters Patent is hereby corrected as shown below:

Title Page,
Item [75] Inventor: Werner Ziegler, Graz, Austria

Signed and Sealed this

Twenty-fifth Day of September, 2001

Attest:

*Nicholas P. Godici*

NICHOLAS P. GODICI
*Attesting Officer*    Acting Director of the United States Patent and Trademark Office